United States Patent
Ishikawa

(10) Patent No.: US 10,258,237 B2
(45) Date of Patent: Apr. 16, 2019

(54) PHOTOBIOMEDICAL MEASUREMENT APPARATUS

(75) Inventor: Akihiro Ishikawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 573 days.

(21) Appl. No.: 14/363,345

(22) PCT Filed: Jan. 10, 2012

(86) PCT No.: PCT/JP2012/050223
§ 371 (c)(1),
(2), (4) Date: Jul. 15, 2014

(87) PCT Pub. No.: WO2013/105209
PCT Pub. Date: Jul. 18, 2013

(65) Prior Publication Data
US 2014/0330109 A1    Nov. 6, 2014

(51) Int. Cl.
*A61B 5/00*    (2006.01)
*A61B 5/06*    (2006.01)
(Continued)

(52) U.S. Cl.
CPC ............ *A61B 5/0042* (2013.01); *A61B 5/055* (2013.01); *A61B 5/061* (2013.01);
(Continued)

(58) Field of Classification Search
CPC ... A61B 8/0816; A61B 8/4416; A61B 5/0059; A61B 5/04008; A61B 5/0476;
(Continued)

(56) References Cited

U.S. PATENT DOCUMENTS 7,720,519 B2 * 5/2010 Ruohonen ................. A61N 2/02
                                                          382/128
2007/0282189 A1 * 12/2007 Dan .................... A61B 5/0059
                                                          600/407
(Continued)

FOREIGN PATENT DOCUMENTS

JP    2003-88528    3/2003
JP    2007-315827    12/2007

OTHER PUBLICATIONS

PCT/JP2012/050223, International Search Report and Written Opinion mailed Jan. 31, 2012, 4 pages—Japanese, 11 pages—English.
"Factos affecting the accuracy of near-infrared spectroscopy concentration calculations for focal changes in oxygenation parameters", G. Strangman, et al./NeuroImage 18 (2003), Academic Press, 1053-8119/03/$-see front mater © 2003 Elsevier Science (USA), www.elsevier.com/locate/ynimg, pp. 865-879, 15 pages—English.
(Continued)

*Primary Examiner* — Angela M Hoffa
*Assistant Examiner* — Vani Gupta
(74) *Attorney, Agent, or Firm* — Andrew F. Young, Esq.; Lackenbach Siegel, LLP

(57) ABSTRACT

A photobiomedical measurement apparatus includes a measurement point determination module to determine a specified position in a brain surface image as a measurement point by designating the specified position in the brain surface image with an input device, an estimated point determination module to determine a specific position in a scalp surface image as an estimated point(s) based on the measurement point (m) and displaying an image of the estimated point (s); and a position-guiding module that displays, on the scalp surface image pathway images (L1, L2), which represent the shortest pathways along the scalp surface between the estimated point (s) and reference points on the scalp surface image corresponding to reference points of the subject.

10 Claims, 7 Drawing Sheets

(51) Int. Cl.
*A61B 5/055* (2006.01)
*G01R 33/48* (2006.01)
*A61B 5/1455* (2006.01)

(52) U.S. Cl.
CPC ........ *A61B 5/14553* (2013.01); *A61B 5/0035* (2013.01); *A61B 5/0082* (2013.01); *A61B 5/06* (2013.01); *A61B 5/4064* (2013.01); *A61B 5/742* (2013.01); *A61B 5/743* (2013.01); *A61B 2576/026* (2013.01); *G01R 33/4808* (2013.01)

(58) Field of Classification Search
CPC ..... A61B 5/055; A61B 5/4064; A61B 5/4088; A61B 5/4094; A61B 5/4848; A61B 2576/026; A61B 5/0035; A61B 5/0042; A61B 5/0082; A61B 5/14553; A61B 5/742; A61B 5/743; A61B 5/06; A61B 5/061; G01R 33/4808
See application file for complete search history.

(56) References Cited

U.S. PATENT DOCUMENTS

2008/0051651 A1\* 2/2008 Yamamoto ............... A61B 8/08 600/437
2015/0342461 A1\* 12/2015 Ishikawa ............. A61B 5/0059 600/409

OTHER PUBLICATIONS

"Three-dimensional probabilistic anatomical cranio-cerebral correlation via the international 10-20 system oriented for transcranial functional brain mapping", M. Okamoto, et al./NeuroImage 21 (2004), Elsevier, 1053-8119/03/$-see front mater © 2003 Elsevier Inc., www.elsevier.com/locate/vnimg, pp. 99-111, 13 pages—English.

\* cited by examiner (a)

(b)

(c)

PHOTOBIOMEDICAL MEASUREMENT APPARATUS

CROSS REFERENCE TO RELATED APPLICATIONS

This application claims priority from and relates to International App. Ser. No.: PCT/JP2012/050223 filed Jan. 10, 2012, the entire contents of which are incorporated herein by reference.

FIGURE SELECTED FOR PUBLICATION

FIG. 3

BACKGROUND OF THE INVENTION

Field of the Invention

The present invention relates to a photobiomedical measurement apparatus. More particularly, the present invention provides a photobiomedical measurement apparatus that noninvasively measures a brain activity.

Description of the Related Art

Industrial applications of the present invention provide a photobiomedical measurement apparatus that noninvasively measures brain activities.

To date, a brain function photo imaging apparatus that can conveniently and noninvasively measure a brain activity using light has been developed. According to such a brain function photo imaging apparatus, a light emission probe arrayed on the subject's scalp surface radiates near infrared (IR) light having three (3) different wave lengths $\lambda_1$, $\lambda_2$, $\lambda_3$ (e. g. 780 nm, 805 nm and 830 nm) and a light receiving probe arrayed on the scalp surface detects a light intensity, $A(\lambda_1)$, $A(\lambda_2)$, $A(\lambda_3)$ (information of an amount of received light) of near infrared light having each wave length $\lambda_1$, $\lambda_2$, $\lambda_3$ emitted from the brain.

Simultaneous equations showed as the relational equations (1), (2) and (3) are set using e. g. Modified Beer Lambert Law to obtain a product [oxyHb] of oxyhemoglobin concentration and light path length and a product [deoxyHb] of deoxyhemoglobin and light path length in the cerebral blood flow from $A(\lambda_1)$, $A(\lambda_2)$, $A(\lambda_3)$, the information of the amount of received light obtained in this manner, and then the simultaneous equations are solved (refer to Non-Patent Document 1, hereby incorporated fully by reference). In addition, a product ([oxyHb]+[deoxyHb]) of total hemoglobin concentration and light path length is calculated from the product [oxyHb] of oxyhemoglobin concentration and light path length and the product [deoxyHb] of deoxyhemoglobin and light path length.

$$A(\lambda_1) = E_o(\lambda_1) \times [\text{oxy}Hb] + E_d(\lambda_1) \times [\text{deoxy}Hb] \quad (1)$$

$$A(\lambda_2) = E_o(\lambda_2) \times [\text{oxy}Hb] + E_d(\lambda_2) \times [\text{deoxy}Hb] \quad (2)$$

$$A(\lambda_3) = E_o(\lambda_3) \times [\text{oxy}Hb] + E_d(\lambda_3) \times [\text{deoxy}Hb] \quad (3)$$

Meantime, $E_o(\lambda_m)$ is an absorbance coefficient of oxyhemoglobin at the light having wavelength $\lambda_m$ and $E_d(\lambda_m)$ is an absorbance coefficient of deoxyhemoglobin at the light having wavelength $\lambda_m$.

Here, a relationship between the distance (channel), between the light emission probe and the light receiving probe, and the measurement region is illustrated. FIG. 6 is a cross section view illustrating a relationship between a pair of a light emission probe and a light receiving probe and a measurement region.

The light emission probe 12 is pushed to a light emission point t of the scalp surface of a subject and further a light receiving probe 13 is pushed to a light receiving point r of the scalp surface of the subject. And light is radiated from the light emission probe 12 and light emitted from the scalp surface is incident on the light receiving probe 13. At this time, light radiated from the emission point on the scalp surface t and light thereof passing the banana-shape (measurement area, see FIG. 6) reaches to the light receiving point r of the scalp surface. Accordingly, $A(\lambda_1)$, $A(\lambda_2)$, $A(\lambda_3)$, the information of the amount of the received light as to the measurement region m at the depth that is half of the distance of the shortest line along the scalp surface of the subject particularly between the light emission point t and the light receiving point r from the midpoint s of the shortest line along the scalp surface of the subject particularly between the light emission point t and the light receiving point r among the measurement areas can be obtained.

Meantime, a measurement region m is a brain region but there is the scalp skin existing outside of the brain so that, unfortunately, such as a medical doctor and/or a laboratory technician cannot determine the arrayed position of the light emission probe 12 and the light receiving probe 13 while confirming the brain position.

Therefore, the medical doctor and/or the laboratory technician determines the arrayed position of the light emission probe 12 and the light receiving probe 13 based on the reference point set on the scalp surface but, unfortunately, they do not determine the arrayed position of the light emission probe 12 and the light receiving probe 13 based on the brain position. In addition, for example, the International 10-20 System Law is known as the reference points set on the scalp surface (see e. g. Non-Patent Document 2, the entire contents of which are herein incorporated by reference).

However, unfortunately, the human-brain shape is actually skewed and unsymmetrical in many humans. Therefore, despite unsymmetrical human brain, when the brain activity is measured at where the positions of the arrayed position of the light emission probe 12 and the light receiving probe 13 are arrayed evenly as to the scalp surface, it is further problematic that the brain activity of the brain region to be measured would not be measured.

In addition, the anatomical structure of individual brain is different from person to person. Specifically, since the brain shapes are different from person to person in many cases, the brain activity data measured based on the International 10-20 System Law could not been compared among plural people.

So, a photobiomedical measurement apparatus is disclosed in which a 3-dimensional configuration image can be image-displayed to show the positional relationship between scalp surface and brain surface to array a light emission probe 12 and a light receiving probe 13 and so forth. (See e. g. Patent Document 1, the entire contents of which are incorporated herein by reference.) FIG. 7 is a figure showing 3-dimensional configuration image showing the positional relationship between scalp surface and brain surface. Such photobiomedical measurement apparatus comprises a configuration image display means image-displaying 3-dimensional configuration image showing the positional relationship between a scalp surface image and a brain surface image, a measurement point determination means determining the predetermined point of the brain surface image as the measurement point m by designating a predetermined position of the brain surface image, and an estimated point determination means determining the specified point of the scalp surface image as an estimated point s and further image-displaying the estimated point s.

Therefore, according to such a photobiomedical measurement apparatus as proposed, such as a medical doctor and/or a laboratory technician can accurately array a light emission probe 12, a light receiving probe 13 and so forth while monitoring an image-display of a 3-dimensional configuration image showing the positional relationship between a scalp surface image and a brain surface image.

PRIOR ARTS

Patent Document

Patent Document 1: Laid Open JP 2007-315827

Non-Patent Document

Non-Patent Document 1: Factors affecting the accuracy of near-infrared spectroscopy concentration calculations for focal changes in oxygenation parameters, NeuroImage 18, 865-879, 2003
Non-Patent Document 2: "Three-dimensional probabilistic anatomical cranio-cerebral correlation via the international 10-20 system oriented for transcranial functional brain mapping" (NeuroImage 21 (2004) 99-111)

ASPECTS AND SUMMARY OF THE INVENTION

Aspects to be Solved

However, the photobiomedical measurement apparatus described above can image-display an estimated point on the scalp surface image, but there is no mark on subject's scalp surface so that it can be difficult to decide accurately the position of subject's scalp surface corresponding to the estimated point s. As results, information of an amount of received light, A ($\lambda_1$), A ($\lambda_2$), A ($\lambda_3$) as to the measurement point m might not be obtained in case because a light emission probe 12 and a light receiving probe 13 and so forth could not be arrayed accurately on the subject's scalp surface.

Means to Solve the Objects

The inventor of the present invention studied a method to decide accurately a position of subjects' scalp surface corresponding to the estimated point s to solve the above problem. Then, the inventor found utilizing a reference point set on scalp surface by such as the International 10-20 System Law.

Specifically, a photobiomedical measurement apparatus of the present invention is a photobiomedical measurement apparatus comprising a display apparatus to conduct an image-display, and an input apparatus to conduct an input operation; a measurement point determination module to determine the predetermined position of the brain surface image as a measurement point, in which a predetermined position of an image-displayed brain surface image is specified by the input apparatus based on 3-dimensional configuration image data showing a positional relationship between scalp surface and brain surface; an estimated point determination module to determine a specified position of the image-displayed scalp surface image based on the 3-dimensional configuration image data and further display an image of the estimated point on the scalp surface image based on the measurement point; and a position-guiding module to display an pathway image on the scalp surface image, showing the shortest pathway between the estimated point and the reference point of the scalp surface image corresponding to the reference point of the subject along the scalp surface.

Here, "3-dimensional configuration image data showing a positional relationship between scalp surface and brain surface" is a 3-dimensional configuration image data generated by extracting a video image data showing scalp surface and brain surface from subjects' video image data generated by such as a nuclear magnetic resonance image diagnosis apparatus (hereinafter MRI) or from a CT image (refer to FIG. 7.)

Further, a "reference point" is a point and so forth specified by the International 10-20 System Law, may include, for example, nasal root (Nasion=Nz), occipital protuberance (Inion=Iz) and right-and-left bipreauricular points (AL, AR).

Further, a "measurement point" is any point designated on the brain surface image by using such as an input device and may include, for example, motor area, somesthetic area, visual area, auditory area, and motor speech area.

Further, an "estimated point" is a position determined on scalp surface based on a measurement point and may include, for example, a position of scalp surface image in the shortest distance from the measurement point and center of gravity coordinate of brain surface expanding the radius of the sphere and scooped out by the sphere.

According to a photobiomedical measurement apparatus of the present invention, an estimated point on scalp surface image is determined by designating a measurement point on a brain surface image so that a pathway image showing the shortest distance between the estimated point and the reference point of the scalp surface image corresponding to subject's reference point can be displayed on the scalp surface image. Accordingly, a medical doctor and/or laboratory technician can decide the position of subjects scalp surface, corresponding to the estimated point, while referring to the pathway image from the subjects reference point.

Effects of the Invention

As described above, according to a photobiomedical measurement apparatus of the present invention, a position of subject's scalp surface, corresponding to the estimated point, can be accurately decided so that a light emission probe and a light receiving probe and so forth can be accurately arrayed.

Means to Solve Other Problems and Effects Thereof

Further, a photobiomedical measurement apparatus of the present invention, may also include a configuration image data acquisition module to acquire a scalp surface configuration image data by extracting a configuration video image data showing scalp surface and further a brain surface configuration image data by extracting a configuration video image data showing brain surface based on a configuration video image data showing the subject, including scalp surface and brain surface; and a configuration image generation module to generate the 3-dimensional configuration image data by synthesizing the scalp surface configuration image data and the brain surface configuration image data.

As described above, according to a photobiomedical measurement apparatus of the present invention, 3-dimensional configuration image data showing a positional relationship between scalp surface and brain surface is generated so that the accurate positional relationship between scalp surface and brain surface can be shown.

Further, according to a photobiomedical measurement apparatus of the present invention, the position-guiding module may display the shortest distance along scalp surface between the estimated point and the reference point of the scalp surface image corresponding to the subject's reference point.

As described above, according to a photobiomedical measurement apparatus of the present invention, the shortest distance between the estimated point and the reference point is displayed so that the position of subject's scalp surface, corresponding to the estimated point, can be more accurately decided.

Further, according to a photobiomedical measurement apparatus of the present invention, the reference point of the subject may be nasal root, top of head, right preauricular point or left preauricular point.

Further, according to a photobiomedical measurement apparatus of the present invention, the estimated point determination module may determine the specific position of the scalp surface image located in the shortest distance from the estimated point as the estimated point.

Then, a photobiomedical measurement apparatus of the present invention may include a measurement probe having at least one light emission probe arrayed on the scalp surface and at least one light receiving probe arrayed on the scalp surface, from which the light emission probe radiates light to the scalp surface and by which the light receiving probe detects emitted light from the scalp surface.

According to a photobiomedical measurement apparatus of the present invention, a brain activity of the brain region to be measured can be measured regardless the individual variation of anatomical structure of brain thereof.

Further, a photobiomedical measurement apparatus of the present invention may include a configuration video image data acquisition module to acquire the configuration video image data and the configuration video image data acquisition module may acquire a configuration video image data generated by a nuclear magnetic resonance image (MRI) diagnosis apparatus.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
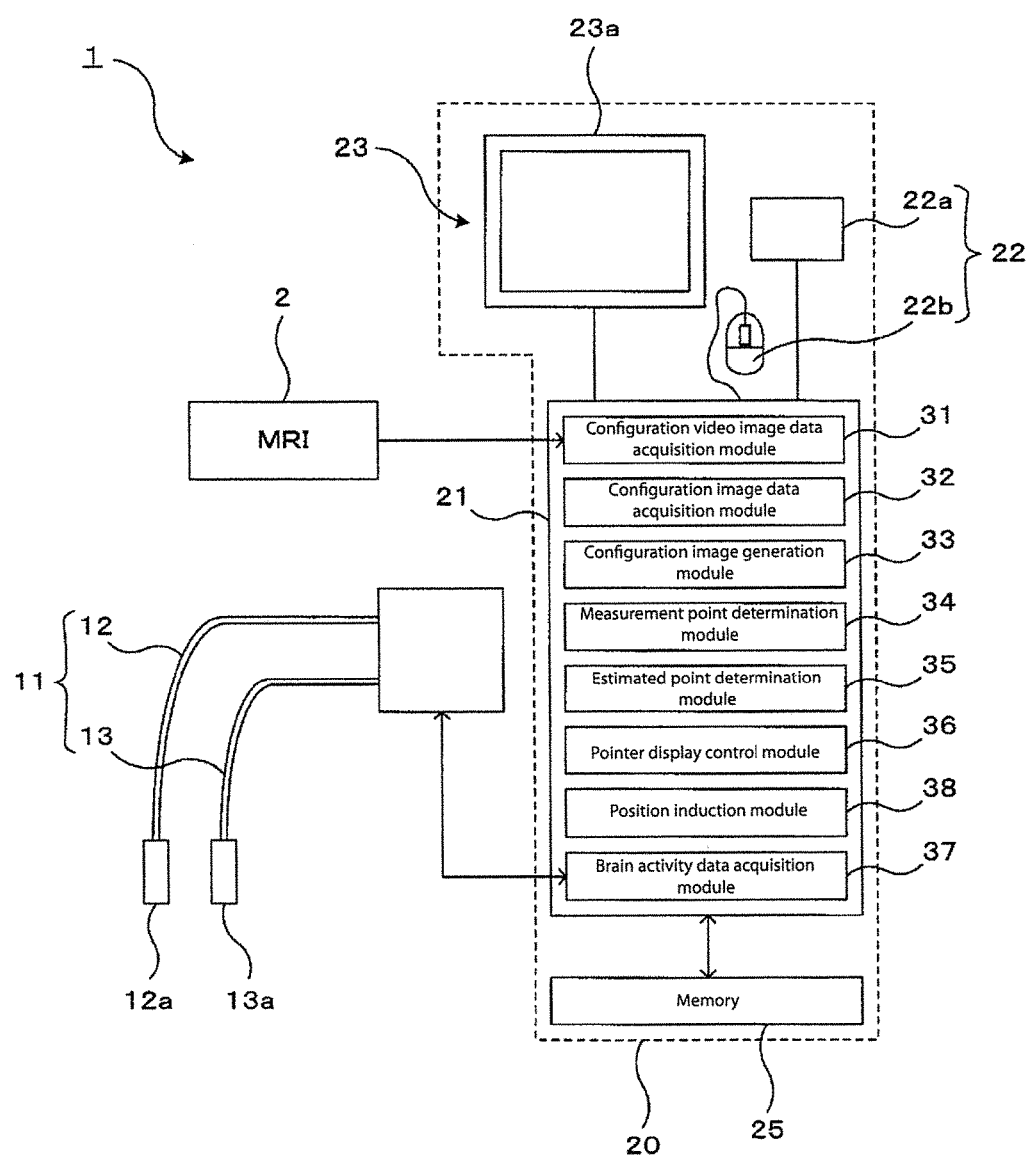
FIG. 1 is a block diagram showing an aspect of one alternative embodiment of a photobiomedical measurement apparatus of the present invention.

Reference will now be made in detail to embodiments of the invention. Wherever possible, same or similar reference numerals are used in the drawings and the description to refer to the same or like parts or steps. The drawings are in simplified form and are not to precise scale. The words 'couple' 'connected' 'linked' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. It will be further understood that certain terms, such as 'data' may be plural or singular a suited to the circumstance, and that there shall be no limitation on such use, so that 'a data' or 'the data' or simply 'data' may be plural or singular. These and similar directional terms should not be construed to limit the scope in any manner. It will also be understood that other embodiments may be utilized without departing from the scope of the present invention, and that the detailed description is not to be taken in a limiting sense, and that elements may be differently positioned, or remotely located (and operable via distant electronic connection) or otherwise noted as in the appended claims without need of the written description being required thereto.

Various operations may be described as multiple discrete operations in turn, in a manner that may be helpful in understanding embodiments of the present invention; however, the order of description should not be construed to imply that these operations are order dependent.

FIG. 1 is a block diagram showing an aspect of one alternative and exemplary embodiment of a photobiomedical measurement apparatus of the present invention.

A photobiomedical measurement apparatus 1 is constituted from a nuclear magnetic resonance image diagnosis apparatus (hereinafter MRI) 2, a measurement probe 11 and a computer 20 controlling an entire photobiomedical measurement apparatus 1.

Figure 2:
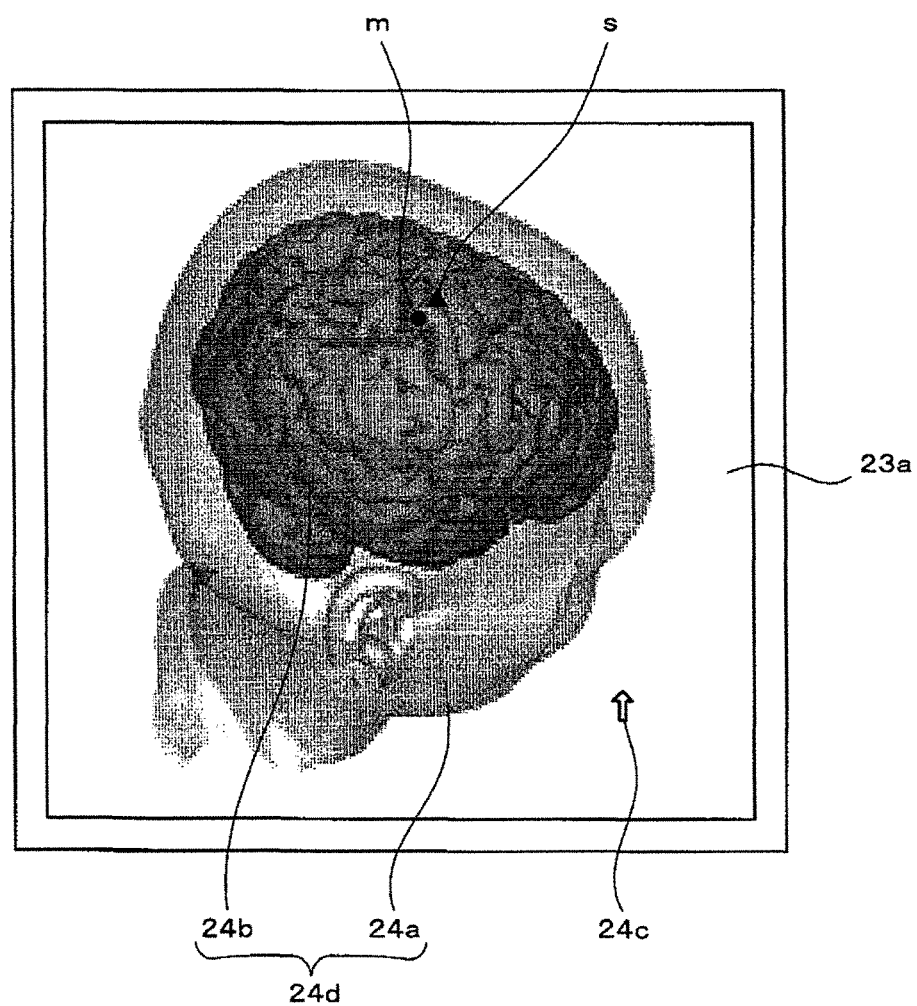
FIG. 2 is a figure illustrating one embodiment of a monitor screen displaying an image obtained from a photobiomedical measurement apparatus.
Figure 3:
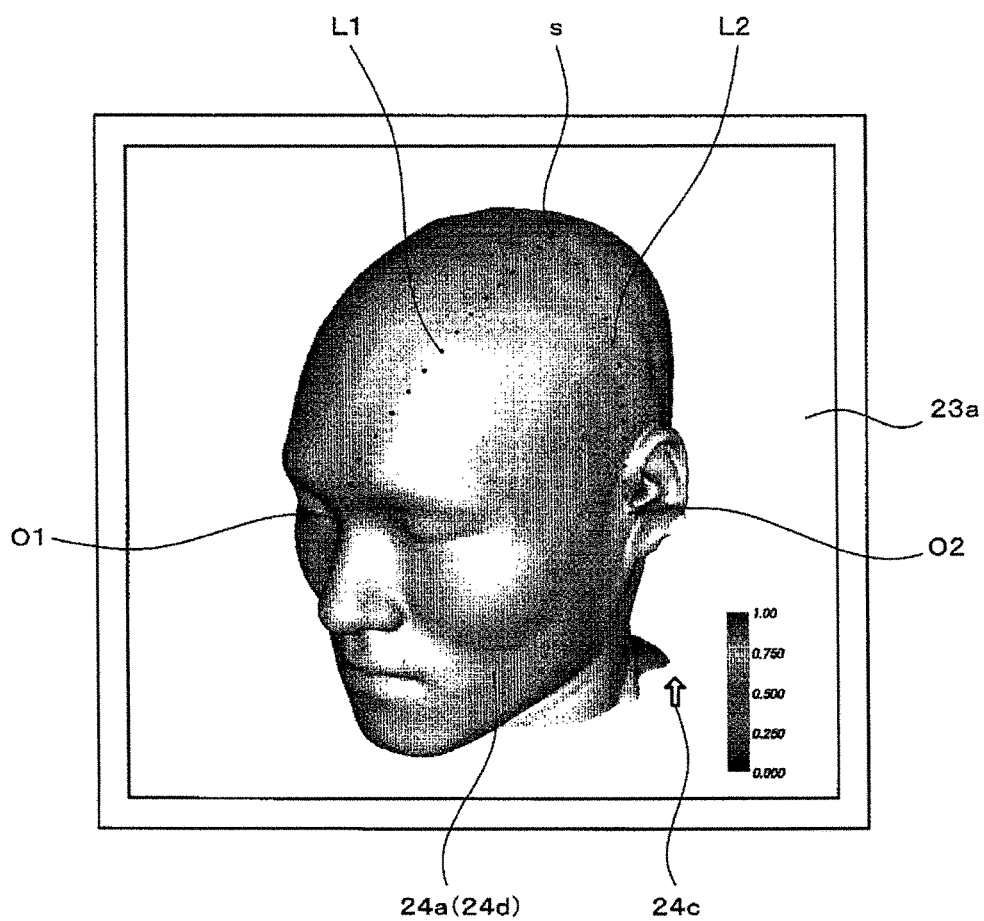
FIG. 3 is a figure illustrating one embodiment of a monitor screen displaying an image obtained from a photobiomedical measurement apparatus.

FIG. 2 and FIG. 3 are figures illustrating one embodiment of a monitor screen 23a image-displaying an image obtained from a photobiomedical measurement apparatus 1. FIG. 2 is a figure illustrating an image-display of a 3-dimensional configuration image 24d showing a positional relationship between a scalp surface image 24a and a brain surface image 24b. In addition, images of a pointer 24c, a measurement point m and an estimated point s are image-displayed. In addition, the scalp surface 24a is displayed as a translucent image. FIG. 3 is a figure illustrating an image-display of a 3-dimensional configuration image 24d showing a scalp surface image 24a. Further, pathway images L1, L2 are image-displayed.

Figure 4:
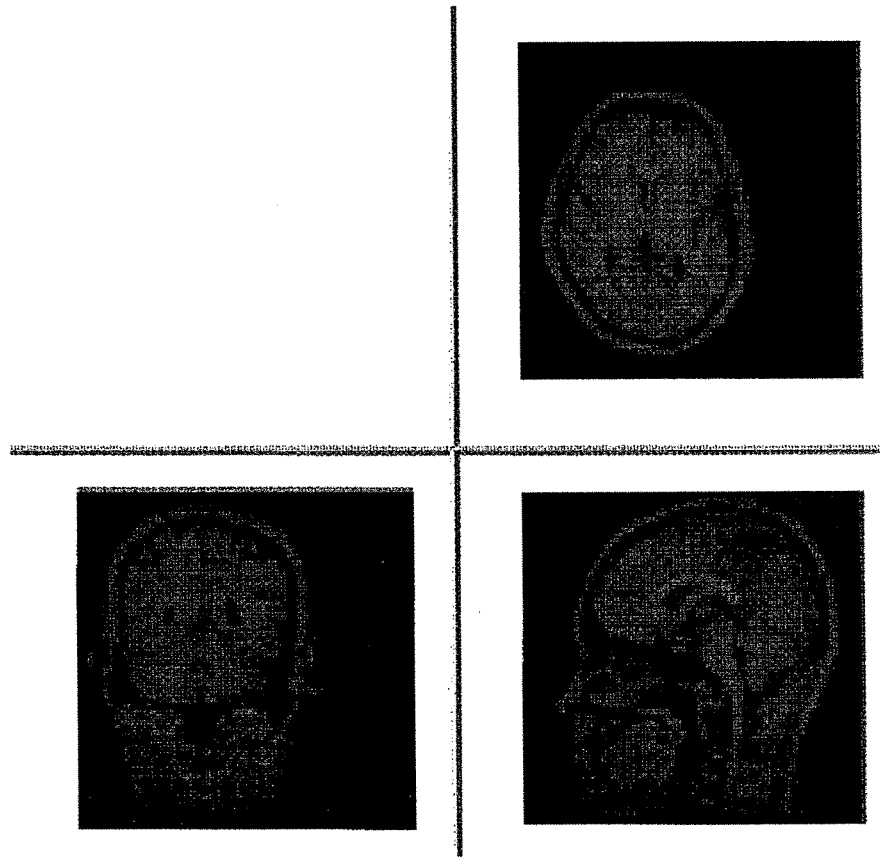
FIG. 4 is a figure illustrating a two-dimensional image in three directions, obtained by MRI.

As shown in FIG. 4, MRI 2 generates configuration video image data showing a 2-dimensional original image in three directions. Further, the configuration video image data show a subject, including scalp surface and brain surface thereof. Further, the configuration video image data are constituted from plural pixels having numerous values as to strength information, phase information and so forth of MR signals.

A measurement probe 11 has a light emission probe 12 and a light receiving probe 13. The light emission probe 12 radiates light according to a driving signal input from a computer 20. The light receiving probe 13 outputs information of an amount of received light, A ($\lambda_1$), A ($\lambda_2$), A ($\lambda_3$), to the computer 20.

The computer 20 having CPU 21, as well as all the other required components for normal operation of a computer containing a process controller incorporated therein for operative use, additionally connects a memory 25 for memorizing configuration video image data, scalp surface configuration video image data, brain surface configuration data and brain activity data; a display device 23 having a monitor screen 23a and so forth; a keyboard, touch screen interface, or other user interface device of any kind as an input device and a mouse 22b as a further type of input device. It will be understood herein, that the phrase 'input device' will be broadly interpreted to include additionally and optionally computer 20, CPU 21, the memory, the measurement probe 11, or any related input device, and shall not be limited to a particular type of input device (e.g., a keyboard, or a mouse, or a touch-screen), as will be understood by those of skill in the art of designing biomedical measurement devices.

Further, the functions processed by CPU 21 are illustrated as blocks, including a configuration video image data acquisition module 31, a configuration image data acquisition module 32, a configuration image generation module 33, a measurement point determination module 34, an estimated point determination module 35, a pointer display control module 36, a position-guiding module 38 and a brain activity data acquisition module 37.

The pointer display control module 36 conducts an image-display of the pointer 24c on the monitor screen 23a and further conducts controls of movements of the pointer 24c image-displayed on the monitor screen 23a and designation of the position with the pointer 24c, based on the input signal output from the mouse 22b, or other input device.

The configuration video image data acquisition module 31 acquires a configuration video image data generated by MRI 2 and further conducts a control of memorizing the configuration video image data in the memory 25.

The configuration image data acquisition module 32 acquires scalp surface configuration image data by extracting the configuration image data showing scalp surface and further acquires brain surface configuration image data by extracting the configuration video image data showing brain surface based on the configuration video image data memorized in the memory 25, and further conducts a control of memorizing the scalp surface configuration video image data and the brain surface configuration video image data in the memory 25.

A method for the above extraction may include, for a non-limiting example, an image region splitting method such as a region expansion method, a region merging method and a heuristic method, by using plural pixels having numeric values such as strength information and phase information of MRI; a method for extracting a region by connecting boundary elements; and a method for extracting a region by deforming a closed curve. In this way, the scalp surface configuration video image data and the brain surface configuration video image data are acquired by extracting the configuration video image data so that clear image data can be obtained.

A configuration image generation module 33 generates a 3-dimensional configuration image 24d showing the positional relationship between the scalp surface image 24a and the brain surface image 24b by synthesizing the scalp surface configuration video image data and the brain surface configuration video image data, which are memorized in the memory 25; and conducts a control of conducting an image-display of the 3-dimensional configuration video image 24d on the screen monitor 23a. At this time, when the brain surface image 24a and the brain surface image 24b are overlappingly displayed, the scalp surface image 24a is image-displayed as translucent. Further, the scalp surface configuration image data and the brain surface configuration image data are synthesized based on the configuration video image data so that the 3-dimensional configuration image 24d can accurately show the positional relationship between scalp surface and brain surface.

The pointer 24c designates the predetermined position of the brain surface image 24b image-displayed on the monitor screen 23a so that the measurement point determination module 34 can specify the predetermined position of the brain surface image 24b as a measurement point in and conduct a control of conducing the image-display of the measurement point m on the brain surface image 24b on the monitor screen 23a.

The estimated point determination module 35 specifies a specific position of the scalp surface image 24a image-displayed on the monitor screen 23a for the estimated point s based on the measurement point m and further conducts a control of the monitor screen 23a to conduct an image-display of the estimated point s on the scalp surface image 24a. At this time, the estimated point determination module 35 specifies, for example, a specific position of the scalp surface image 24a in the shortest distance from the measurement point m as the estimated point s. Further, the estimated point determination module 35 may determine the center of gravity coordinate of brain surface expanding the radius of the sphere and scooped out by the sphere as the estimated point s.

The predetermined positions of two locations of the scalp surface image 24a image-displayed on the monitor screen 23a are designated by the pointer 24c so that the position-guiding module 38 may specify the predetermined positions of two locations of the scalp surface image 24a as each reference point O1, O2 and further conduct a control to image-display a pathway image L1 showing the shortest pathway along scalp surface between the estimated point s and the reference point O1 and a pathway image L2 showing the shortest pathway along scalp surface between the estimated point s and the reference point O2 on the monitor screen 23a.

The above described reference point may include, for example, an image of nasal root, an image of top of head, an image of right preauricular area and the image of left preauricular area. Further, a generation method for the above pathway image L1, L2 may include, for example, the method that re-constitutes a top of head cross section of a plane including an estimated point s and a reference point and calculates the distance of outer layer pixels between an estimated point s and a reference point, and the method that obtains a corresponding point to scalp surface of the middle point of line passing an estimated point s and a reference point and further a corresponding point to scalp surface of the middle point of line passing the estimated point s (reference point) and a corresponding point, and repeatedly obtain these to provide the pathway.

A brain activity data acquisition module 37 outputs a driving signal for acquiring brain activity data to a light emission probe 12 based on an input signal output from an input device 22 and further conducts controlling for memorizing the brain activity into the memory 25 by being input information of an amount of received light, A ($\lambda_1$), A ($\lambda_2$), A ($\lambda_3$), from a light receiving probe 13. Accordingly, a product ([oxyHb]+[deoxyHb]) of total hemoglobin concentration and light path length, for example, is obtained from the product [oxyHb] of oxyhemoglobin concentration and light path length and the product [deoxyHb] of deoxyhemoglobin and light path length, using the brain activity data.

Figure 5:
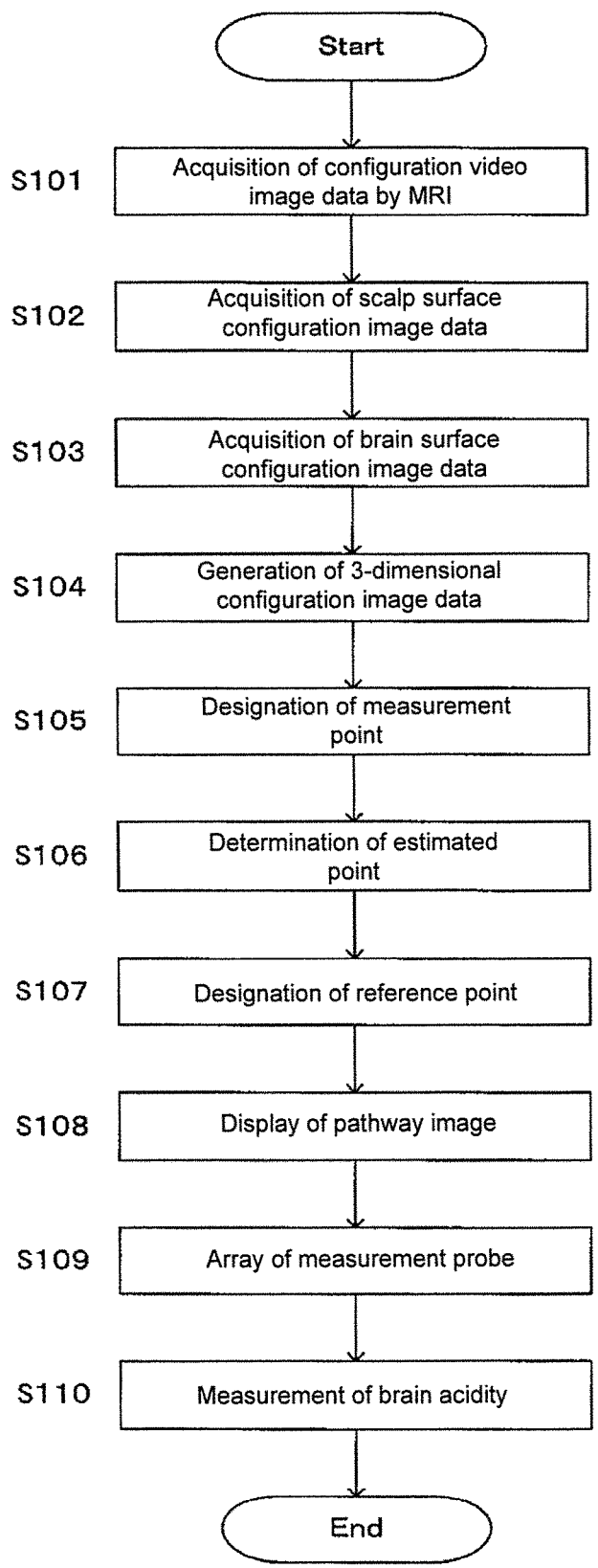
FIG. 5 is a flow diagram illustrating an examination method relates to a photobiomedical measurement apparatus of the present invention.

Here, the present invention illustrates an examination method for a brain activity of regions of brain according to a photobiomedical measurement apparatus 1 of the present invention. FIG. 5 is a flow diagram illustrating one embodiment of the examination method using a photobiomedical measurement apparatus 1.

First, a process of step S101 is to acquire a configuration video image data showing a subject, including scalp surface and brain surface, from MRI 2 and further to memorize the configuration video image data in a memory 25 (refer to FIG. 4.) At this time, the configuration video image data may be memorized in a memory 25 by using memory media and so forth from a MRI set in somewhere else.

Next, a process of step S102 is to acquire a scalp surface configuration image data by extracting a configuration video image data showing the scalp surface based on the configuration video image data memorized in the memory 25 and further memorizes the scalp surface configuration image data in the memory 25. At this time, a configuration video image data showing the scalp surface is extracted by using, for example, a surface rendering method (refer to FIG. 7(a)). Next, a process of step S103 is to acquire a brain surface configuration image data by extracting a configuration video image data showing the brain surface based on the configuration video image data memorized in the memory 25 and further memorizes the scalp surface configuration image data in the memory 25. At this time, a configuration video image data showing the brain surface is extracted by using, for example, a volume rendering method (refer to FIG. 7(b)).

Figure 7:
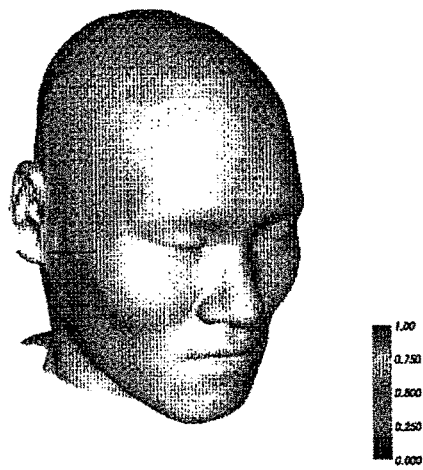
FIG. 7 shows figures illustrating a 3-dimensional configuration image showing the relationship between scalp surface and brain surface.
Figure 7:
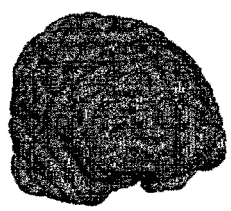
Figure 7:
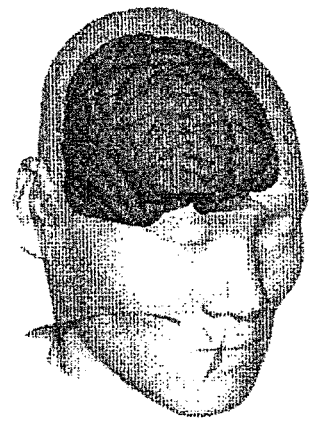

Next, a process of step S104 is to generate a 3-dimensional configuration image 24d showing the positional relationship between the scalp surface image 24a and the brain surface image 24b by synthesizing the scalp surface configuration video image data and the brain surface configuration video image data, which are memorized in the memory 25; and conducts an image-display of the 3-dimensional configuration video image 24d on the screen monitor 23a (refer to FIG. 7(c)).

Next, a process of step S105 is to determine a predetermined position of the brain surface image 24b as a measurement point in by designating the predetermined position of the brain surface image 24b image-displayed on the monitor screen 23a by using a pointer 24c. At this time, an image-display of the measurement point m is conducted on the monitor screen 23a (refer to FIG. 2.) A predetermined position may include, for example, motor area, somesthetic area, visual area, auditory area, and motor speech area. Specifically, a brain activity of predetermined position can be measured.

Next, a process of step S106 is to conduct specifying the specific position of the scalp surface image 24a image-displayed on the screen 23a as an estimated point s based on the measurement point m. At this time, an image-display of the estimated point s is conducted on the monitor screen 23a (refer to FIG. 2).

Next, a process of step S107 is to designate the predetermined positions of two locations of the scalp surface image 24a image-displayed on the monitor screen 23a by the pointer 24c so that the predetermined positions of two locations of the scalp surface image 24a are determined as each reference point O1, O2.

Next, a process of step S108 is to conduct an image-display of a pathway image L1 showing the shortest pathway along scalp surface between the estimated point s and the reference point O1 and a pathway image L2 showing the shortest pathway along scalp surface between the estimated point s and the reference point O2 (refer to FIG. 3).

Next, a process of step S109 is to array a light emission probe 12 and a light receiving probe 13 on a subject so that the middle point of the shortest line along the scalp surface, connecting the position where one end 12a of the probe 12 is arrayed and the position where one end 13a of the probe 13, is the same position as the position of the scalp surface corresponding to the estimated point s. Specifically, a measurement probe 11 is arrayed while referring to the monitor screen 23a image-displaying as shown in FIG. 3.

Figure 6:
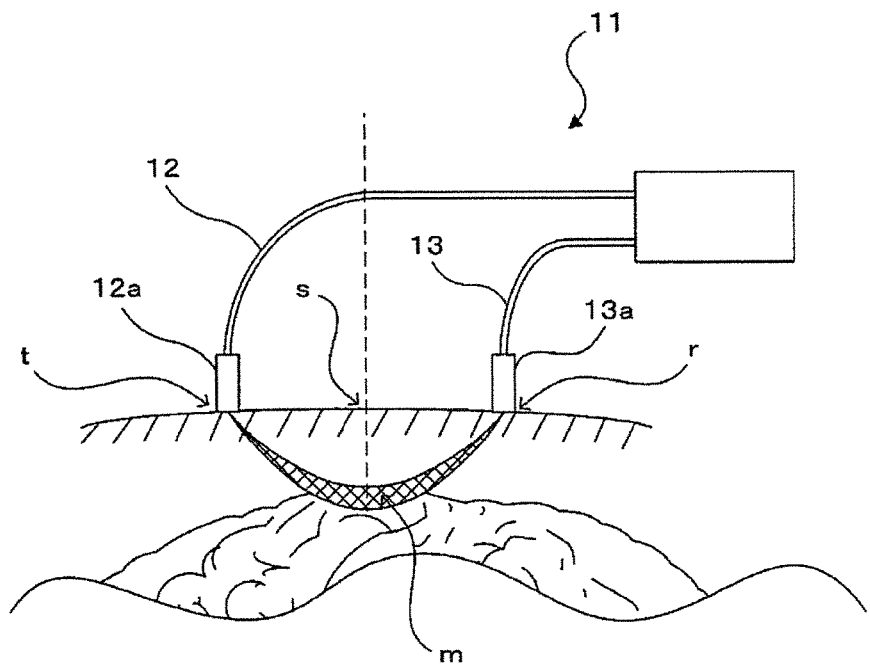
FIG. 6 is a cross section view illustrating the relationship a pair of a light emission probe and a light receiving probe and a measurement point.

Next, a process of step S110 is to radiate light from one end 12a of the light emission probe 12 and further detect the light emitted from the scalp surface at one end 13a of the light receiving probe 13. At this time, light moves from the light emission point t of scalp surface to the light receiving point of scalp surface passing through a brain position corresponding to the measurement point m of the brain surface image 24b (refer to FIG. 6.) Accordingly, a product ([oxyHb]+[deoxyHb]) of total hemoglobin concentration and light path length, the product [oxyHb] of oxyhemoglobin concentration and light path length and the product [deoxyHb] of deoxyhemoglobin and light path length of the brain position corresponding to the measurement point of the brain surface image 24b are obtained.

And then, when the process of the step S110 is completed, the present flow diagram shall end.

As described, according to a photobiomedical measurement apparatus 1 of the present invention, a position of subject's scalp surface, corresponding to the estimated point, can be accurately decided so that a light emission probe 12 and a light receiving probe 13 can be accurately arrayed.

Other Embodiments (1) The above X-ray examination apparatus 1 comprises a measurement probe 11 having one light emission probe 12 and one light receiving probe 13, but may comprise a measurement probe having a number of grid light emission probes and light receiving probes in lieu of the measurement probe 11.

At this time, the middle point of the shortest line along the scalp surface, connecting the position where a light emission probe is arrayed and the position where a light receiving probe, is the same position as plural estimated points as far as possible.

(2) The above X-ray examination apparatus 1 comprises an MRI, but may comprise CT and so forth in lieu of MRI, according to and without departing from the scope and spirit of the present invention having been understood by those of skill in the art.

(3) The above X-ray examination apparatus 1 comprises an image-display of a pathway image L1 showing the shortest pathway along scalp surface between the estimated point s and the reference point O1 and a pathway image L2 showing the shortest pathway along scalp surface between the estimated point s and the reference point O2, but instead, may comprise an image-display of a numeric value showing the shortest distance along scalp surface between the estimated point s and the reference point O1 and a numeric value showing the shortest distance along scalp surface between the estimated point s and the reference point O2.

(4) The above X-ray examination apparatus 1 comprises a position-guiding module 38 designates the predetermined positions of two locations of the scalp surface image 24a by the pointer 24c so that the predetermined positions of two locations of the scalp surface image 24a are determined as each reference point O1, O2 but may specify the predetermined positions of two (or three) locations of the scalp surface image as each reference point by automatically detecting and selecting two (or three) locations near the estimated point s among the points designated by such as the International 10-20 System Law.

For example, the position-guiding module automatically extracts a reference point (e. g. a point designated by such as the International 10-20 System Law) by the feature-point detection device using the normalization pattern recognition method, and calculates the distance between plural extracted reference points and a target point (estimated point s), respectively. According to such calculation, the reference points, 2 or 3, having a short distance are automatically selected.

Accordingly, such as a medical doctor and/or a laboratory technician may not need to designate the reference point by using a pointer.

(5) The above X-ray examination apparatus 1 comprises a position-guiding module 38 specifies the predetermined positions of two locations of the scalp surface image 24a by the pointer 24c so that the predetermined positions of two locations of the scalp surface image 24a are determined as each reference point O1, O2, but also may mandatorily specify nasal root (Nasion=Nz), occipital protuberance (Inion=Iz) and right-and-left bipreauricular points (AL, AR) as a reference point.

Accordingly, such as a medical doctor and/or a laboratory technician may not need to designate the reference point by using a pointer.

INDUSTRIAL APPLICABILITY

The present invention can be applied to a photobiomedical measurement apparatus that noninvasively measures brain activities.

It will also be understood, that as used herein the phrases 'being exposed' or 'treating a surface' or 'treating' or 'exposing' or 'illuminating' are understood as the application of irradiative wavelengths on a material, and such treatment may penetrate the full depth of the material or any portion thereof.

It will be understood that the environment proximate that treatment surface is not limited.

It will be further understood by those of skill in the arts, after having studied the disclosure herein, that the modules, computer, and features herein are operative and effective to achieve the noted result without departing from the scope herein, whereby as a non-limiting example, an image module for generating an image from data contains all the needed operative functions, such as processor controls, memory devices, operative software, input/output features, and otherwise effective to render the proposed aspects herein fully operative within the scope and spirit of the present invention.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGN

1: Photobiomedical measurement apparatus
2: MRI
11: Measurement probe
12: Light emission probe
13: Light receiving probe
22: Input device
23: Display device
31: Configuration video image data acquisition module
32: Configuration image data acquisition module
33: Configuration image generation module
34: Measurement point determination module
35: Estimated point determination module
38: position-guiding module
t: Light emission point
r: Light receiving point
m: Measurement point
s: Estimated point

What is claimed is:

1. A photobiomedical measurement apparatus, comprising:
    a display device that conducts an image-display of a subject;
    an input device that designates an input to said photobiomedical measurement apparatus;
    a computer, having a central processing unit (CPU), configured to
    specify a predetermined position of a brain surface image as a measurement point by designating said predetermined position of an image-displayed brain surface image based on a 3-dimensional configuration image data showing a positional relationship between a scalp surface and a brain surface by using said input device;
    determine a position of the image-displayed scalp surface image based on said 3-dimensional configuration image data and the measurement point as an estimated point;
    cause the display device to display the estimated point on the scalp surface image; and
    cause the display device to display a pathway image showing the shortest pathway along the scalp surface between said estimated point and a reference point of the scalp surface image corresponding to a reference point of said subject on said scalp surface image.

2. The photobiomedical measurement apparatus, according to claim 1, wherein the computer, having the central processing unit (CPU), is further configured to:
    acquire a scalp surface configuration image data by extracting a configuration video image data showing said scalp surface, and further acquire a brain surface configuration image data by extracting a configuration video image data showing said brain surface, based on a configuration video image data showing the subject, including said scalp surface and said brain surface; and
    generate said 3-dimensional configuration image data by synthesizing said scalp surface configuration image data and said brain surface configuration image data.

3. The photobiomedical measurement apparatus, according to claim 1, wherein:
said reference point is one of a nasal root, an occipital protuberance, a right bipreauricular point, and a left bipreauricular point.

4. The photobiomedical measurement apparatus, according to claim 1, wherein the computer, having a central processing unit (CPU), is further configured to:
determine a position of said scalp surface image in a shortest distance from said measurement point as the estimated point.

5. The photobiomedical measurement apparatus, according to claim 1, further comprising:
at least one measurement probe having at least one light emission probe arrayed on said scalp surface and at least one light receiving probe arrayed on said scalp surface; and
said light emission probe irradiates a light onto said scalp surface and said light receiving probe detects a light emitted from said scalp surface.

6. The photobiomedical measurement apparatus, according to claim 2, further comprising the computer, having the central processing unit (CPU), is further configured to:
acquire said configuration video image showing the subject and including said scalp surface and said brain surface, and
wherein said configuration video image data showing the subject and including said scalp surface and said brain surface is generated by a nuclear magnetic resonance image diagnosis apparatus.

7. The photobiomedical measurement apparatus, according to claim 2, wherein:
said reference point is one of a nasal root, an occipital protuberance, a right bipreauricular point, and a left bipreauricular point.

8. The photobiomedical measurement apparatus, according to claim 7, wherein the computer, having the central processing unit (CPU), is further configured to:
determine a position of said scalp surface image in a shortest distance from said measurement point as the estimated point.

9. A photobiomedical measurement system, comprising:
a display device conducting an image-display;
a computer, having a central processing unit (CPU), configured to;
specify a predetermined position of a brain surface image as a measurement point by designating said predetermined position of an image-displayed brain surface image based on a 3-dimensional configuration image data showing a positional relationship between a scalp surface and a brain surface using an input device;
determine a position of the image-displayed scalp surface image based on the 3-dimensional configuration image data and cause an image-display of an estimated point on the scalp surface image, based on the measurement point, on the display device;
cause the display device to display a pathway image, on said scalp surface image between the estimated point and a reference point of the scalp surface image corresponding to a reference point of the subject, and further cause the display device to show a shortest pathway between the estimated point and the reference point along the scalp surface;
acquire a scalp surface configuration image data by extracting a configuration video image data showing a scalp surface and further acquire a brain surface configuration image data by extracting a configuration image data showing brain surface based on a configuration video image data showing the subject, including scalp surface and brain surface; and
generate said 3-dimensional configuration image data by synthesizing said scalp surface configuration image data and said brain surface configuration image data.

10. A method for operating a photobiomedical measurement system, comprising the steps of:
providing a display device conducting an image-display;
providing a computer having a central processing unit (CPU), configured to:
specify a predetermined position of a brain surface image as a measurement point by a step of designating said predetermined position of an image-displayed brain surface image based on an acquired 3-dimensional configuration image data showing a positional relationship between a scalp surface and a brain surface using an input device;
determine a position of the image-displayed scalp surface image based on the 3-dimensional configuration image data and cause an image-display of an estimated point on the scalp surface image, based on the measurement point, on the display device;
cause the display device to display a pathway image, on said scalp surface image between the estimated point and a reference point of the scalp surface image corresponding to a reference point of the subject, and further cause the display device to show a shortest pathway between the estimated point and the reference point along the scalp surface;
acquire a scalp surface configuration image data by extracting a configuration video image data showing a scalp surface and further acquire a brain surface configuration image data by extracting a configuration image data showing brain surface based on a configuration video image data showing the subject, including scalp surface and brain surface; and
generate said 3-dimensional configuration image data by synthesizing said scalp surface configuration image data and said brain surface configuration image data.

* * * * *